United States Patent [19]

Monguzzi et al.

[11] 4,178,444
[45] Dec. 11, 1979

[54] HYDRAZONO DERIVATIVES OF CEPHALOSPORINS

[75] Inventors: Riccardo Monguzzi, Corsico; Giorgio Pifferi, Milan; Mario Pinza, Corsico; Giampietro Broccali, Milan, all of Italy

[73] Assignee: CRAF Sud, Aprilia Latina, Italy

[21] Appl. No.: 913,475

[22] Filed: Jun. 7, 1978

[30] Foreign Application Priority Data

Jun. 7, 1977 [IT] Italy ................................ 24436 A/77

[51] Int. Cl.$^2$ .................... C07D 501/36; C07D 501/32
[52] U.S. Cl. ........................................ 544/30; 544/22; 544/24; 544/25; 544/26; 544/27; 544/28; 260/347.3; 560/34; 549/77
[58] Field of Search .................. 544/24, 25, 26, 27, 544/28, 30

[56] References Cited

U.S. PATENT DOCUMENTS 3,971,778  7/1976  Cook et al. ............................ 544/25
3,998,950  12/1976  Broggi et al. ........................... 544/30

OTHER PUBLICATIONS

Morrison et al. "Organic Chemistry", p. 633, (1966).

*Primary Examiner*—David Wheeler
*Attorney, Agent, or Firm*—Stevens, Davis, Miller & Mosher

[57] ABSTRACT

Hydrazono derivatives of cephalosporins of the formula

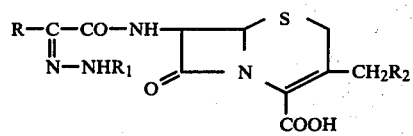

wherein R is phenyl optionally substituted, 2- or 3-thienyl optionally substituted, or 2- or 3-furyl optionally substituted, $R_1$ is hydrogen or alkyl having from 1 to 4 carbon atoms, and $R_2$ is hydrogen, acetoxy, carbamoyloxy or a heterocyclic nucleus preferably bounded through a sulphur atom to the methylene group. The compounds have bactericidal activity. Methods of preparation are also disclosed.

5 Claims, No Drawings

HYDRAZONO DERIVATIVES OF CEPHALOSPORINS

The present invention relates to hydrazono derivatives of cephalosporins having marked antibiotic activity and to the preparation thereof. The hydrazono derivatives of the present invention have the structural formula:

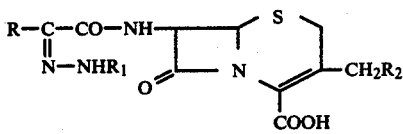

wherein
R is phenyl optionally substituted, 2- or 3- thienyl optionally substituted or 2- or 3- furyl optionally substituted,
$R_1$ is hydrogen or an alkyl having from 1 to 4 carbon atoms, and
$R_2$ is hydrogen, acetoxy, carbamoyloxy, or a heterocyclic nucleus preferably bounded through a sulphur atom to the methylene group.

The compounds of formula I can, depending upon the planar structure of the hydrazono group, present a Z(sin) or E(anti) configuration or may be a mixture of the two forms Z and E. The present invention also comprises the pharmaceutically acceptable salts of the compounds of formula I with alkali metals, alkalino-earth metals, or with suitable organic bases and the corresponding esters easily hydrolyzable which are transformed into the free acid by means of hydrolysis in vivo.

Among the salts with alkali metals the sodium and potassium salts are particularly preferred, and among the organic bases amines, such as procain, N,N-dibenzylethylendiamine and dibenzylamine are particularly preferred.

Among the heterocyclic nuclei, 1,3,4,-thiadiazol-2-yl optionally substituted, 1,2,3,4-tetrazol-5-yl optionally substituted, and pyridyl optionally substituted are preferred. Among the substituents of the heterocyclic nucleus lower alkyl radicals, particularly the methyl radical, are preferred.

Among the esters hydrolyzable in vivo, the pivaloyloxymethyl ester and 1-(ethoxycarbonyloxy) ethyl ester are preferred.

According to the present invention the compounds of formula I are prepared by condensation of 7-aminocef-3-em-4-oic-3-substituted acid of the formula

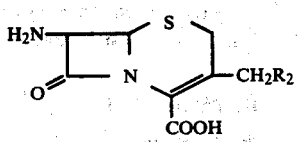

wherein $R_2$ has the above meaning, suitably protected at the carboxylic group, with a protected and activated derivative of α-hydrazonacetic acid of the formula

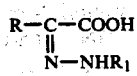

wherein R and $R_1$ have the above meanings.

The condensation reaction takes place in an aprotic solvent in the presence of an organic base at a temperature between −5° C. and room temperature. The protected derivative of α-hydrazono acetic acid III reacts in activated form, preferably as 2,4-dinitrophenyl ester and in this case the organic base is a tertiary amine, such as for example dimethylpiperazine. As protecting groups of the carboxylic group of the 7-aminocef-3-em-4-oic acid, t-butyl, p.methoxybenzyl, 2,4,6-trimethylbenzyl and benzhydryl are generally used. As protecting groups of the hydrazonic group, t.butoxycarbonyl 4-nitrobenzyloxycarbonyl and p.methoxybenzyloxycarbonyl are generally used.

The introduction of the heterocyclic ring in position 3 of the cefem nucleus can be carried out also following condensation with derivative of α-hydrazonacetic acid. In this case the condensation takes place between the protected 7-aminocephalosporanic acid and the activated and protected derivative of the α-hydrazonacetic acid; the protecting groups are removed and the radical acetyloxy in position 3 is replaced with the desired heterocyclic nucleus.

A suitable aprotic solvent is a cyclic ether such as, for example, dioxane, tetrahydrofuran or acetonitrile.

At the end of the condensation the protecting groups of the carboxylic and hydrazonic group are removed from the desired cephalosporanic compound through methods known, per se, and the final compounds I preferably isolated from the reaction mixture as salts of alkali metals, particularly in the form of sodium salts. The compounds III are themselves novel and can, in their turn, be conveniently prepared starting from a suitable derivative of the glyoxylic acid by reaction with a derivative of hydrazine and successive introduction of the protecting group at the hydrazonic nitrogen. Alternatively, such compounds can be obtained by directly reacting the derivative of the starting glyoxylic acid with the suitably protected hydrazine derivative.

As an alternative to the method described above, the compounds of formula I can be prepared by direct condensation of the 3-substituted 7-aminocef-3-em-4-oic acid, suitably protected at the carboxyl, with a derivative of α-hydrazonacetic acid and successively removing the protecting group at the carboxyl group. The reaction is carried out in an aprotic solvent preferably consisting of a cyclic ether such as tetrahydrofuran and dioxane in the presence of a condensing agent such as for example dicyclocarbodiimide and ethoxyacetylene. Also in this alternative the introduction of the heterocyclic ring in position 3 of the nucleus cephem can be carried out following condensation with the derivative of α-hydrazonacetic acid. In such a case, the condensation takes place between the protected 7-aminocephalosporanic acid and the derivative of α-hydrazonacetic acid and therefore the radical acetyloxy at position 3 is replaced in a known manner with the desired heterocyclic nucleus. Compounds of formula I have antibacteric activity especially against gram-positive microorganisms including some penicillinase-producers. They are also valuably active against gram-negative microorganisms. The minimum inhibiting concentration (MIC) in vitro of the compounds of the present invention has been evaluated for some microorganisms, expressed in γ/ml and the experimental results obtained are shown in the following Table.

All the products of the invention are resistant to acids and do not lose their biological activity even after treatment for one hour with hydrochloric acid N/20.

|  | Compound of EXAMPLE 2 | Compound of EXAMPLE 4 | Compound of EXAMPLE 5 | EXAMPLE 1 |
| --- | --- | --- | --- | --- |
| Staphylococcus aureus pen. - sens. str. 1 | 1.56 | 0.78 | 0.39 | 0.78 |
| Staphylococcus aureus pen. - sens. str. 2 | 3.12 | 0.39 | 0.39 | 1.56 |
| Staphylococcus aureus pen. - resist. str. 3 | 3.12 | 1.56 | 1.56 | 1.56 |
| Staphylococcus aureus pen. - resist. str. 4 | 6.25 | 6.25 | 6.25 | 6.25 |
| Streptococcus pyogenes | 0.19 | 0.19 | 0.095 | 0.095 |
| Streptococcus pneumoniae | 0.19 | 0.19 | 0.095 | 0.095 |
| Sarcina lutea | 0.78 | 0.19 | 0.39 | 0.78 |
| Bacillus subtilis | 0.048 | 0.095 | 0.19 | 0.19 |
| Escherichia coli | 6.25 | 6.25 | 12.5 | 6.25 |
| Shigella dysenteriae | 12.5 | 3.12 | 12.5 | 12.5 |
| Salmonella typhi | 25 | 6.25 | 25 | 12.5 |
| Salmonella typhimurium | 100 | 50 | 100 | 100 |
| Pseudomonas aeruginosa | >200 | >200 | >200 | >200 |

EXAMPLE 1

Sodium salt of (Z)7-(α-methylhydrazonophenylacetamido) cephalosporanic acid

Sixteen and one half grams of methylhydrazine hydrochloride are added to a solution of 30 g phenylglyoxylic acid in 200 ml N sodium hydroxide. The mixture is kept under stirring for three hours and by filtration under vacuo 14.7 g (Z)-α-methylhydrazonophenylacetic acid melting at 106°–107° C. are obtained.

To a solution formed by 26 g t. butylester of 7-aminocephalosporanic acid and 16.34 g dicyclohexylcarbodiimide in 390 ml tetrahydrofuran, a solution of 14.11 g (Z)-α-methylhydrazonophenylacetic acid in 100 ml tetrahydrofuran is added dropwise. The mixture is left under stirring for five hours, then filtered and the filtrate is concentrated under vacuo to dryness. The residue is dissolved in ethyl acetate, washed with a solution of sodium bicarbonate, with hydrochloric acid and finally with water, then made anhydrous; the solvent is removed under vacuo and the residue taken up with 90 ml trifluoroacetic acid and 45 ml anisole. The reaction mixture is stirred for 90 minutes at room temperature, concentrated under vacuo to dryness; the residue is slurried from ethyl ether, taken up with a dilute solution of sodium bicarbonate, extracted with methylene chloride and ethyl acetate is added to the aqueous phase, acidifying to pH 1 with hydrochloric acid. The organic phase is separated, washed with distilled water, made anhydrous and after filtration a solution of 1,1 M sodium ethylhexanoate in isopropyl alcohol is added. The resulting mixture is concentrated under vacuo to dryness and the residue is slurried from isopropyl alcohol, obtaining 6.75 g sodium salt of (Z)7-(α-methylhydrazonophenylacetamido)cephalosporanic acid melting at 164°–166° C. (with decomposition). Rf 0,49 (silica gel - eluent:acetone - acetic acid 95:5).

EXAMPLE 2

Sodium salt of (E)7-(α-methylhydrazonophenylacetamido) cephalosporanic acid

The mother liquors coming from the filtration of (Z)-α-methylhydrazonophenylacetic acid give, after standing overnight in a refrigerator, a precipitate which by crystallization from ethyl acetate gives 1.23 g (E)-α-methylhydrazonophenylacetic acid melting at 133°–135° C. (with decomposition). Operating in an analogous manner to that described in the preceding Example, the sodium salt of (E)7-(α-methylhydrazonophenylacetamido) cephalosporanic acid melting at 153°–157° C. with decomposition is obtained. Rf 0.47 (silica gel - eluent:acetone -acetic acid 95:5).

EXAMPLE 3

Sodium salt of (Z)N-/7-(α-methylhydrazonophenylacetamido)/3-{/5-methyl-1,3,4-thiadiazol-2-yl)thio/methyl}ceph-3-em-4-oic acid To a suspension of 1 g sodium salt of (Z)7-(α-methylhydrazonophenylacetamido) cephalosporanic acid prepared as described above and 0.38 g 5-methyl-2-mercapto-1,3,4-thiadiazol in 12 ml buffered solution at pH 6.5 are added 0.23 g sodium bicarbonate. The reaction mixture is heated under stirring at 55° C. for 6 hours, diluted with water, acidified to pH 1 with hydrochloric acid, then filtered under vacuo and the product still damp is taken up with a dilute solution of sodium bicarbonate, extracted with methylene chloride, separating the aqueous phase to which ethyl acetate is added and acidifying to pH 1 with hydrochloric acid. The organic phase is separated, washed with water, made anhydrous and after filtration a 1,1 M solution of sodium ethylhexanoate in isopropanol is added. The mixture is concentrated under vacuo to dryness and the residue is slurried from isopropyl alcohol. 0.37 grams of sodium salt of (Z)N-/7-(α-methylhydrazonophenylacetamido/3-{/(5-methyl-1,3,4-thiadiazol-2-yl)thio/methyl}ceph-3-em-4-oic acid melting at 171°–173° C. (with decomposition) are obtained. Rf 0.38 (silica gel - eluent:acetone - acetic acid 95:5).

EXAMPLE 4

Sodium salt of (Z)N-/7-(α-methylhydrazonophenylacetamido)/-3-{/(1-methyl-1,2,3,4-tetrazol-5-yl)thio/methyl}ceph-3-em-4-oic acid Operating in a manner analogous to that described in Example 3 and using 1-methyl-2-mercapto-1,3,4,5-tetrazol, the sodium salt of (Z)N-/7-(α-methylhydrazonophenylacetamido/-3-{/(1-methyl-1,2,3,4-tetrazol-5-yl) thio/methyl}ceph-3-em-4-oic acid melting at 188°–193°

C. (with decomposition) is obtained. Rf 0,38 (silica gel - eluent:acetone - acetic acid 95:5).

EXAMPLE 5

Sodium salt of Z(N)-/7-(α-methylhydrazonophenylacetamido)/3-{/(5-methyl-1,3,4,thiadiazol-2-yl)thio/methyl} ceph-3-em-4-oic acid To a solution formed by 5 g t.butyl ester of 7-amino-3{/5-methyl-1,3,4,thiadiazol-2-yl)thio/methyl} ceph-3-em-4-oic acid and 2.99 g dicyclohexylcarbodiimide in 100 ml tetrahydrofuran is added dropwise a solution of 2,58 g (Z)α-methylhydrazonophenylacetic acid in 75 ml tetrahydrofuran. Proceeding in a manner analogous to that previously described 0.65 g sodium salt (Z)N-/7-(α-methylhydrazonophenylacetamido)/-3{/(5-methyl-1,3,4-thiadiazol-2-yl)thio/methyl}ceph-3-em-4-oic are obtained, in the form of a dark-yellow colored amorphous product melting at 171°–173° C. (with decomposition). Rf 0.38 (silica gel - eluent:acetone - acetic acid 95:5).

EXAMPLE 6

Sodium salt of (Z)N-/7-(α-methylhydrazonophenylacetamido)/-3-{/(1-methyl-1,2,3,4-tetrazol-5-yl)thio/methyl}ceph-3-em-4-oic acid Operating in a manner analogous to that described above the sodium salt of (Z)N-/7-(α-methylhydrazonophenylacetamido)/-3-{/(1-methyl-1,2,3,4-tetrazol-5-yl)thio/methyl}ceph-3-em-4-oic acid melting at 188°–192° C. (with decomposition) is obtained. Rf=0.38 (silica gel, eluent:acetone, acetic acid 95:5).

EXAMPLE 7

(Z)7-(α-hydrazonophenylacetamido)cephalosporanic acid

A solution of 232.2 g 4-nitrobenzyl chloroformiate in 500 ml tetrahydrofuran is slowly poured into a solution consisting of 165 g 4-nitrobenzyl alcohol and 161.9 ml triethylamine in 165 ml anhydrous tetrahydrofuran, cooled to 0° C.

It is heated to room temperature and stirred for 2 hours, filtered under vacuo from insoluble tetraethylamine chloride and concentrated under vacuo to dryness. The residue is slurried from 2000 ml ethyl ether, obtaining 184 g bis(4-nitrobenzyl)carbonate melting at 156°–158° C. Then, 184 grams of bis(4-nitrobenzyl)carbonate, and 30.44 g hydrazine hydrate dissolved in 1800 ml acetonitrile are refluxed under stirring overnight. The boiling solution is filtered, cooled to room temperature and acidified to Congo red by addition of a solution of hydrochloric acid in ethyl ether.

The hydrochloride is collected under vacuo, dissolved in 1500 ml water, filtered, the filtrate adjusted to pH 9.5/10 with 30% sodium hydroxide. The precipitate is collected under vacuo, dried under vacuo and dissolved in 5 ml acetonitrile. It is acidified to Congo red and 75 g N(4-nitrobenzyloxycarbonyl)hydrazine hydrochloride are collected under vacuo, melting at 212°–213° C. (with decomposition). To a solution consisting of 39.3 phenylglyoxylic acid and 262 ml M sodium hydroxide in 800 ml water are added 65 g N(4-nitrobenzyloxycarbonyl)hydrazine hydrochloride under stirring at room temperature.

It is kept under stirring for 2 hours, filtered and dried under vacuo to obtain 87 g 2-[N(4-nitrobenzyloxycarbonylhydrazono)phenyl]acetic acid as a mixture of isomers. It is taken up with 1600 ml ethyl acetate, refluxed under stirring for one hour, kept under stirring at room temperature overnight and after filtration, 53 g (E)2-(4-nitrobenzyloxycarbonylhydrazono)phenyl acetic acid are obtained, melting at 189°–190° C.; Rf 0.44 (silica gel - eluent:acetone - acetic acid 95:5). The filtrate is concentrated under vacuo to dryness and the residue slurried from diethyl ether to give 22.76 g (Z)2-[N(4-nitrobenzyloxycarbonylhydrazono)phenyl]acetic acid, melting at 178°–179° C.; Rf 0.79 (silica gel - acetone:acetic acid 95:5).

A solution of 3.14 g (Z)2-(4-nitrobenzyloxycarbonylhydrazono)phenyl acetic acid in 30 ml anhydrous tetrahydrofuran is slowly poured under stirring at 0° C. into a solution consisting of 3 g 3-acetoxymethyl-7-aminocef-3-em-4-carboxylic acid and 1.89 g dicyclohexylcarbodiimide in 40 ml anhydrous tetrahydrofuran. It is kept under stirring for 2 hours at 0° C. and then at room temperature overnight. It is filtered under vacuo and the filtrate is concentrated under vacuo to dryness, the residue is taken up with 100 ml water and 100 ml ethyl ether, the mixture is cooled to 0° C., acidified to pH 1, kept under stirring for 30 minutes at 0° C. and by filtration under vacuo 4.3 g t.butylester of (Z)3-acetoxymethyl-7-[α-(4-nitrobenzyloxycarbonylhydrazono)-phenylacetamido}ceph-3-em-4-oic acid are obtained, melting at 104°–106° C. Rf 0.67 (silica gel eluent - ethyl acetate: benzene 1:1).

To a cooled and stirred solution of 30 ml trifluoroacetic acid and 10 ml anisole, 4.3 g of the above mentioned product was added. The solution was kept at 0° C. for 90 minutes and then concentrated under vacuo to dryness. The residue was taken up with 20 ml diethyl ether and filtered. 0.5 grams of 3-acetoxymethyl-7-[α-(4-nitrobenzyloxycarbonylhydrazono)phenylacetamido}-ceph-3-em-4-oic acid was obtained, melting at 147° C. (with decomposition). Rf 0.62 (eluent acetone:acetic acid 95:5).

To a solution of 60 mg sodium carbonate in 30 ml water, 0.5 g of the above mentioned product are added and the so formed clear solution is poured into a prehydrogenized suspension of 0.5 g palladium on 5% calcium carbonate. It is hydrogenized at room temperature, filtered under vacuo from the catalyst, cooled to 0° C. and under stirring adjusted to pH 1; the precipitate consisting of 167 mg of (Z)3-acetoxymethyl-7-[α-(hydrazono)phenylacetamido]ceph-3-em-4-oic acid is collected under vacuo, melting at 200°–230° C. (with decomposition). Rf 0.37 (eluent acetonitrile:water 4:1).

The intermediates (E) and (Z)α-[N(4-nitrobenzyloxycarbonylhydrazono)]phenylacetic acid may be also prepared by the following procedure: A solution consisting of 133.8 g sodium salt of 2-hydrazonophenylacetic acid in 2500 ml water and 2500 ml dioxane is cooled to 0° C. and two solutions of 154.93 g of 4-nitrobenzylchloroformiate in 535 ml dioxane and 90.35 g sodium carbonate in 535 ml water are simultaneously added thereto. The mixture is warmed to room temperature and kept under stirring overnight, then it is filtered under vacuo and, concentrated under vacuo till the dioxane is completely removed. It is diluted with 5000 ml water, the pH adjusted to 2, filtered and dried under vacuo. From the isomers mixture are separated 60 g of (E) α[N(4-nitrobenzyloxycarbonylhydrazono)]-phenylacetic acid and 45 g of (Z) α[N(4-nitrobenzyloxycarbonylhydrazono)]phenylacetic acid.

EXAMPLE 8

(E)7-(α-Hydrazonophenylacetamido) cephalosporanic acid

To a solution consisting of 5 g (E)2-(4-nitrobenzyloxycarbonylhydrazono) phenylacetic acid and 2.03 ml triethylamine in 40 ml anhydrous acetone, cooled to 0° C., are added 1.4 ml ethyl chloroformiate and to the resulting suspension, after 15 minutes of stirring at 0° C., is added a cold mixture prepared by the following procedure: A suspension of 3-acetoxymethyl-7-aminoceph-3-em-4-oic acid and 3.51 g bis-trimethylsilylurea in 40 ml anhydrous dichloromethane is refluxed for one hour, cooled to 0° C. and added dropwise to the above mentioned mixed anhydride.

The mixture is kept under stirring at 0° C. for 2 hours and then for a further 2 hours at room temperature, filtered under vacuo, the filtrate concentrated under vacuo to dryness and the residue is taken up with 200 ml 2% sodium bicarbonate. It is extracted with 200 ml ethyl acetate, the aqueous phase is stratified with 100 ml ethyl acetate and acidified to pH 1 at 0° C. with 20% hydrochloric acid. The organic phase is separated, washed with water, made anhydrous and concentrated under vacuo to dryness. The residue is taken up with 30 ml acetone and treated with a solution of M sodium 2-ethylhexanoate to give 3.87 g (Z) 3-acetoxymethyl-7-[α-(4-nitrobenzyloxycarbonylhydrazono)-phenylacetamido]ceph-3-em-4-acid sodium salt, melting at 141°–145° C.; Rf 0.49 (silica gel acetonitrile:water 4:1). The resulting product is dissolved in 150 ml water and added to a pre-hydrogenized suspension of 1.5 g 10% palladium on calcium carbonate. It is hydrogenized at room temperature, filtered under vacuo from the catalyst and the filtrate adjusted to pH 1. The precipitate is taken up under vacuo, obtaining 0.6 g (E)3-acetoxymethyl-7-[α-(hydrazono)phenylacetamido]-ceph-3-em-4-oic acid, melting at 180°–220° C. (with decomposition). Rf 0.39 (silicagel acetone:acetic acid 95:5).

EXAMPLE 9

Sodium salt of (Z)3-carbamoyloxymethyl-7-(α-methylhydrazonophenylacetamido)ceph-3-em-4-oic acid To a solution consisting of 2.4 g 3-carbamoyloxymethyl-7β-aminocef-3-em-4-oic acid benzhydryl ester and 1.12 g dicyclohexylcarbodiimide in 40 ml anhydrous tetrahydrofuran, a mixture containing 0.96 g (Z) 2(methylhydrazono)-2-phenylacetic acid, obtained as previously described, in 5 ml anhydrous tetrahydrofuran is slowly poured under stirring at room temperature. It is kept under stirring at room temperature overnight, filtered under vacuo from dicyclohexylurea and the filtrate is concentrated under vacuo to dryness. The residue is taken up with 57.2 ml cold trifluoroacetic acid and 19 ml anisole, the solution is kept under stirring for one hour at 0° C. concentrated under vacuo to dryness; the residue is taken up with 150 ml 3% sodium bicarbonate, extracted three times with 50 ml ethyl acetate, the aqueous phase is stratified with 50 ml ethyl acetate and acidified to pH 1 with 20% hydrochloric acid. The organic phase is separated, washed with water, made anhydrous over magnesium sulphate and after filtration, concentrated under vacuo to dryness. The residue is taken up with 25 ml acetonitrile and a solution of M sodium ethylhexanoate is added thereto to give 0.6 g (Z)3-carbamoyloxymethyl-7-(α-methylhydrazonophenylacetamido)ceph-3-em-4-oic acid sodium salt melting at 220°–224° C. (with decomposition). Rf 0.33 (silica gel - eluent:acetone:acetic acid 95:5).

EXAMPLES 10 and 11

Operating as above described there were also obtained:

Sodium salt (Z) 3-[(5-methyl-1,3,4-thiadiazol-2-yl)thio]-methyl-7-(α-hydrazonophenylacetamido)ceph-3-em-4-oic acid.

Sodium salt (Z) 3-[(1-methyl-1,2,3,4-tetrazol-5-yl)thio]-methyl-7-[α-(hydrazonophenylacetamido]ceph-3-em-4-oic acid.

We claim:

1. A hydrazonocephalosporin of the formula:

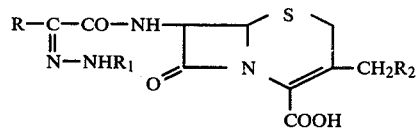

wherein R is selected from the group consisting of phenyl, 2-thienyl, 3-thienyl, 2-furyl, and 3-furyl;

R$_1$ is hydrogen or alkyl having from 1 to 4 carbon atoms; and

R$_2$ is selected from the group consisting of hydrogen, acetoxy, carbamoyloxy; 1,3,4-thiadiazol-2-yl-thio; methyl-substituted 1,3,4-thiadiazol-2-yl; 1,2,3,4-tetrazol-5-yl-thio; methyl-substituted 1,2,3,4-tetrazol-5-yl-thio; and pyrid-1-yl and a corresponding salt of an alkali or alkaline earth metal, procaine, N,N-dibenzylethylendiamine, and dibenzylamine or the pivaloyloxymethyl ester or 1-(ethoxy-carbonyloxy) ethyl ester thereof.

2. A compound according to claim 1 which is the sodium salt of (Z)7-(α-methylhydrazonophenylacetamido) cephalosporanic acid.

3. A compound according to claim 1 which is the sodium salt of (Z)N-/7-(α-methylhydrazonophenylacetamido)/3-[/(5-methyl-1,3,4-thiadiazol-2-yl)thio/methyl]ceph-3-em-4-oic acid.

4. A compound according to claim 1 which is the sodium salt of (Z)N-/7(α-methylhydrazonophenylacetamido)/-3-[/1-methyl-1,2,3,4-tetrazol-5-yl)thio/methyl]ceph-3-em-4-oic acid.

5. A compound according to claim 1 which is the sodium salt of (Z)7-(α-hydrazonophenylacetamido) cephalosporanic acid.

* * * * *

UNITED STATES PATENT AND TRADEMARK OFFICE
CERTIFICATE OF CORRECTION

PATENT NO. : 4,178,444
DATED : December 11, 1979
INVENTOR(S) : Riccardo MONGUZZI et al.

It is certified that error appears in the above-identified patent and that said Letters Patent are hereby corrected as shown below:

Column 8, line 39, change "1,3,4-thiadiazol-2-yl" to
-- 1,3,4-thiadiazol-2-yl-thio --.

Signed and Sealed this

Twenty-ninth Day of April 1980

[SEAL]

Attest:

SIDNEY A. DIAMOND

Attesting Officer

Commissioner of Patents and Trademarks